US00PP29053P2

(12) United States Plant Patent
Misato

(10) Patent No.: US PP29,053 P2
(45) Date of Patent: Mar. 6, 2018

(54) ***MANDEVILLA* PLANT NAMED 'SUNPA 6416'**

(50) Latin Name: *Mandevilla hybrida*
Varietal Denomination: Sunpa 6416

(71) Applicant: Tomoya Misato, Shiga (JP)

(72) Inventor: Tomoya Misato, Shiga (JP)

(73) Assignee: Suntory Flowers, Ltd, Tokyo (JP)

( * ) Notice: Subject to any disclaimer, the term of this patent is extended or adjusted under 35 U.S.C. 154(b) by 0 days.

(21) Appl. No.: 15/530,377

(22) Filed: Jan. 4, 2017

(51) Int. Cl.
*A01H 5/02* (2006.01)

(52) U.S. Cl.
USPC ..... Plt./232

(58) Field of Classification Search
USPC ..... Plt./232
CPC ..... A01H 5/02
See application file for complete search history.

*Primary Examiner* — Kent L Bell
(74) *Attorney, Agent, or Firm* — C. A. Whealy

(57) ABSTRACT

A new and distinct cultivar of *Mandevilla* plant named 'Sunpa 6416', characterized by its vining plant habit; vigorous growth habit; freely branching habit; early and freely flowering habit; long flowering period; and large white-colored flowers.

1 Drawing Sheet

Botanical designation: *Mandevilla hybrida.*
Cultivar denomination: 'SUNPA 6416'.

BACKGROUND OF THE INVENTION

The present invention relates to a new and distinct cultivar of *Mandevilla* plant, botanically known as *Mandevilla hybrida* and hereinafter referred to by the name 'Sunpa 6416'.

The new *Mandevilla* plant is a product of a planned breeding program conducted by the Inventor in Higashiomi, Shiga, Japan. The objective of the breeding program is to create new vining and freely branching *Mandevilla* plants with freely flowering habit and large attractive flowers.

The new *Mandevilla* plant originated from a cross-pollination in Higashiomi, Shiga, Japan in April, 2006 of a proprietary selection of *Mandevilla hybrida* identified as code number 04M-14-5, not patented, as the female, or seed parent with a proprietary selection of *Mandevilla hybrida* identified as code number 04M-14-9, not patented, as the male, or pollen, parent. The new *Mandevilla* plant was discovered and selected by the Inventor as a single flowering plant from within the progeny of the stated cross-pollination in a controlled greenhouse environment in Higashiomi, Shiga, Japan in October, 2007.

Asexual reproduction of the new *Mandevilla* plant by terminal vegetative cuttings in Higashiomi, Shiga, Japan since April, 2009 has shown that the unique features of this new *Mandevilla* plant are stable and reproduced true to type in successive generations.

SUMMARY OF THE INVENTION

Plants of the new *Mandevilla* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Sunpa 6416'. These characteristics in combination distinguish 'Sunpa 6416' as a new and distinct *Mandevilla* plant:

1. Vining plant habit.
2. Vigorous growth habit.
3. Freely branching habit.
4. Early and freely flowering habit.
5. Long flowering period.
6. Large white-colored flowers.

Plants of the new *Mandevilla* can be compared to plants of the female parent selection. Plants of the new *Mandevilla* differ primarily from plants of the female parent selection in the following characteristics:

1. Leaves of plants of the new *Mandevilla* are smoother than leaves of plants of the female parent selection.
2. Plants of the new *Mandevilla* and the female parent selection differ in flower color as plants of the female parent selection have pink-colored flowers.

Plants of the new *Mandevilla* can be compared to plants of the male parent selection. Plants of the new *Mandevilla* differ primarily from plants of the male parent selection in leaf texture as leaves of plants of the new *Mandevilla* are smoother than leaves of plants of the male parent selection.

Plants of the new *Mandevilla* can be compared to plants of the *Mandevilla amabilis*×*Mandevilla boliviensis* 'Sunmandeho', disclosed in U.S. Plant Pat. No. 11,556. In side-by-side comparisons, plants of the new *Mandevilla* differ from plants of 'Sunmandeho' in the following characteristics:

1. Leaves of plants of the new *Mandevilla* have acuminate apices whereas leaves of plants of 'Sunmandeho' have cuspidate apices.
2. Leaves of plants of the new *Mandevilla* are not as glossy as leaves of plants of 'Sunmandeho'.
3. Flower petals of plants of the new *Mandevilla* are obovate and imbricate whereas flower petals of plants of 'Sunmandeho' are orbicular and not imbricate.
4. Plants of the new *Mandevilla* and 'Sunmandeho' differ in flower color as plants of the new *Mandevilla* have light red purple-colored flower throats whereas plants of 'Sunmandeho' have pale yellow-colored flower throats.

BRIEF DESCRIPTION OF THE PHOTOGRAPHS

The accompanying colored photographs illustrate the overall appearance of the new *Mandevilla* plant showing the colors as true as it is reasonably possible to obtain in colored reproductions of this type. Colors in the photographs may differ slightly from the color values cited in the detailed botanical description which accurately describe the actual colors of the new *Mandevilla* plant.

The photograph at the top of the sheet comprises a side perspective view of a typical flowering plant of 'Sunpa 6416' grown in a container.

The photograph at the bottom of the sheet is a close-up view of a typical flower of 'Sunpa 6416'.

DETAILED BOTANICAL DESCRIPTION

The aforementioned photographs and following observations, measurements and values describe plants grown during the summer in 15-cm containers in an outdoor nursery in Higashiomi, Shiga, Japan and under cultural practices typical of commercial *Mandevilla* production. During the production of the plants, day temperatures averaged 25° C. and night temperatures averaged 15° C. Plants were six months old when the photographs and detailed description were taken. In the following description, color references are made to The Royal Horticultural Society Colour Chart, 2007 Edition, except where general terms of ordinary dictionary significance are used.

Botanical classification: *Mandevilla hybrida* 'Sunpa 6416'.

Parentage:

*Female, or seed, parent*.—Proprietary selection of *Mandevilla hybrida* identified as code number 04M-14-5, not patented.

*Male, or pollen, parent*.—Proprietary selection of *Mandevilla hybrida* identified as code number 04M-14-9, not patented.

Propagation:

*Type*.—By terminal vegetative cuttings.

*Time to initiate roots*.—About two weeks at temperatures about 23° C. to 25° C.

*Time to produce a rooted young plant*.—About five to six weeks at temperatures about 23° C. to 25° C.

*Root description*.—Fibrous; typically light brown in color, actual color of the roots is dependent on substrate composition, water quality, fertilizer type and formulation, substrate temperature and physiological age of roots.

*Rooting habit*.—Freely branching; medium density.

Plant description:

*Plant and growth habit*.—Vining plant habit; vigorous growth habit; freely branching habit.

*Plant height* (*with support*).—About 151 cm.

*Lateral branch description*.—Length: About 12 cm. Diameter: About 3.7 mm. Internode length: About 6 cm. Strength: Strong, flexible. Texture: Pubescent, rough. Color, developing: Close to 144C; slightly tinged with close to 34C. Color, fully developed: Close to 146C and eventually, closer to 199A.

Leaf description:

*Arrangement*.—Opposite, simple.

*Length*.—About 11.2 cm.

*Width*.—About 5.1 cm.

*Shape*.—Oblong.

*Apex*.—Acuminate.

*Base*.—Rounded.

*Margin*.—Entire.

*Texture and luster, upper and lower surfaces*.—Pubescent; matte.

*Venation pattern*.—Pinnate, reticulate.

*Color*.—Developing leaves, upper surface: Close to between 143A and 144A. Developing leaves, lower surface: Close to 146B. Fully expanded leaves, upper surface: Close to between 143A and 146A; venation, close to 145B. Fully expanded leaves, lower surface: Close to 146B; venation, close to 145C.

*Petioles*.—Length: About 6.4 cm. Diameter: About 2.1 mm. Texture, upper and lower surfaces: Pubescent. Color, upper and lower surfaces: Close to 144B.

Flower description:

*Flower type and habit*.—Single salverform flowers arranged in axillary racemes; flowers face mostly upright to outwardly; freely flowering habit with about four to six flowers per inflorescence and about 46 flowers developing per plant.

*Natural flowering season*.—Early flowering habit, plants begin flowering about six weeks after planting; long flowering period, plants flower continuously from early summer until late autumn in Japan.

*Flower longevity on the plant*.—About seven to ten days; flowers not persistent.

*Fragrance*.—None detected.

*Flower buds*.—Height: About 7.1 cm. Diameter: About 1.4 cm. Shape: Trullate. Color: Distally, close to 56D; mid-section, close to NN155B; proximally, close to 145C.

*Flowers*.—Appearance: Salverform; flared trumpet, corolla fused and five-parted; flowers roughly star-shaped. Diameter: About 10.7 cm. Depth (length): About 6.4 cm. Throat diameter: About 1.8 cm. Tube length: About 2.9 cm. Tube diameter, proximally: About 3.8 mm.

*Corolla*.—Quantity and arrangement: Five petals arranged in a single whorl and fused towards the base into an elongated tube; petal lobes imbricate. Petal lobe length: About 4.6 cm. Petal lobe width: About 4.4 cm. Petal lobe shape: Obovate, strongly asymmetrical. Petal lobe apex: Rounded; finely undulate. Petal lobe margin: Entire; finely undulate. Petal lobe texture and luster, upper and lower surfaces: Smooth, glabrous; matte. Throat texture: Smooth, glabrous. Tube texture: Smooth, glabrous. Color: Petal lobe, when opening, upper surface: Close to N155B; towards the throat, close to NN155C. Petal lobe, when opening, lower surface: Close to N155B; proximally, close to NN155B. Petal lobe, fully opened, upper surface: Close to NN155C; venation, close to NN155B; color does not change with development. Petal lobe, fully opened, lower surface: Close to NN155C and NN155A. Throat: Distally, close to NN155C; center, close to NN155C blushed with close to 65C; proximally, close to NN155A; venation, close to NN155B. Tube: Distally, close to NN155B; proximally, close to 150D.

*Calyx*.—Quantity and arrangement: Five sepals arranged in a single whorl, fused at the base; calyx, star-shaped. Sepal length: About 4.7 mm. Sepal width: About 2 mm. Sepal shape: Lanceolate. Sepal apex: Acuminate. Sepal margin: Entire. Sepal texture, upper and lower surfaces: Smooth, glabrous. Sepal color, upper surface: Distally, close to 35A; proximally, close to 145B. Sepal color, lower surface: Distally, close to 145B overlain with close to 34B; proximally, close to 144C.

*Peduncles*.—Length: About 4.9 cm. Diameter: About 2.8 mm. Texture: Pubescent. Aspect: Upright to outwardly. Color: Close to 144B.

*Pedicels*.—Length: About 1.6 cm. Diameter: About 2.5 mm. Texture: Pubescent. Aspect: Upright to outwardly. Color: Close to 145A slightly overlain with close to 34D.

*Reproductive organs*.—Stamens: Quantity and arrangement: Typically five; filaments fused to corolla; anthers, connivent. Anther shape: Lanceolate. Anther size: About 1.7 mm by 8 mm. Anther color: Close to 11C. Pollen amount: Moderate. Pollen color: Close to NN155A. Pistils: Quantity: Typically one. Pistil length: About 1.4 cm. Style color: Close to 145C. Stigma shape: Globose. Stigma color: Close to 145B. Ovary color: Close to 144A.

*Seeds and fruits*.—Seed and fruit production have not been observed on plants of the new *Mandevilla*.

Disease & pest resistance: Plants of the new *Mandevilla* have not been noted to be resistant to pathogens and pests common to *Mandevilla* plants.

Garden performance: Plants of the new *Mandevilla* have been observed to tolerate wind, rain and temperatures ranging from about 4° C. to about 30° C.

It is claimed:

1. A new and distinct *Mandevilla* plant named 'Sunpa 6416' as illustrated and described.

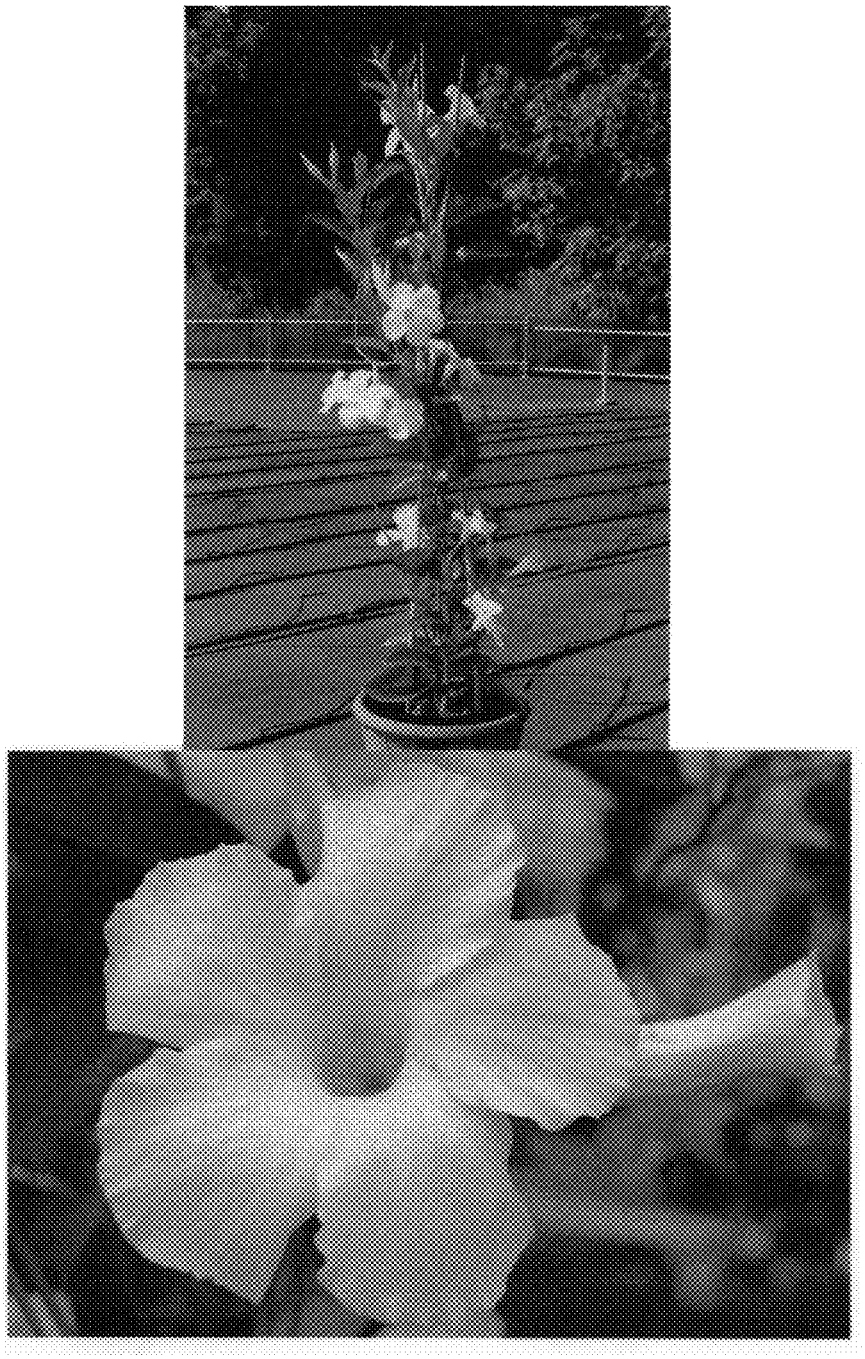

* * * * *